United States Patent
Lan et al.

(10) Patent No.: US 11,054,116 B1
(45) Date of Patent: Jul. 6, 2021

(54) UV PANEL LIGHT

(71) Applicant: SHENZHEN GUANKE TECHNOLOGIES CO., LTD, Shenzhen (CN)

(72) Inventors: Qing Lan, Shenzhen (CN); Ligen Liu, Shenzhen (CN); Shoubao Chen, Shenzhen (CN); Minggui Wang, Shenzhen (CN); Nengsheng Chen, Shenzhen (CN)

(73) Assignee: SHENZHEN GUANKE TECHNOLOGIES CO., LTD, Shenzhen (CN)

( * ) Notice: Subject to any disclaimer, the term of this patent is extended or adjusted under 35 U.S.C. 154(b) by 0 days.

(21) Appl. No.: 17/069,169

(22) Filed: Oct. 13, 2020

(30) Foreign Application Priority Data

Sep. 4, 2020 (CN) .......................... 202021934188.4

(51) Int. Cl.
*F21V 15/01* (2006.01)
*F21V 23/00* (2015.01)
*A61L 9/20* (2006.01)
*F21Y 103/00* (2016.01)

(52) U.S. Cl.
CPC ................ *F21V 15/01* (2013.01); *A61L 9/20* (2013.01); *F21V 23/009* (2013.01); *F21Y 2103/00* (2013.01)

(58) Field of Classification Search
CPC ........... F21V 15/01; F21V 23/009; A61L 9/20
See application file for complete search history.

(56) References Cited

U.S. PATENT DOCUMENTS

| 9,370,600 | B1* | 6/2016 | DuPuis | A61L 9/20 |
| 2002/0080616 | A1* | 6/2002 | Chen | F21V 17/164 |
| | | | | 362/368 |
| 2011/0001060 | A1* | 1/2011 | Welker | F24F 13/078 |
| | | | | 250/455.11 |
| 2012/0320627 | A1* | 12/2012 | Araki | F21S 8/04 |
| | | | | 362/608 |
| 2015/0159839 | A1* | 6/2015 | Howe | F21V 29/505 |
| | | | | 362/311.01 |
| 2016/0136312 | A1* | 5/2016 | Park | F21V 33/0044 |
| | | | | 362/231 |
| 2018/0227999 | A1* | 8/2018 | VandeVelde | F21S 4/28 |
| 2018/0299117 | A1* | 10/2018 | Min | F24F 13/06 |
| 2020/0289698 | A1* | 9/2020 | Polidoro | F21V 21/04 |

* cited by examiner

*Primary Examiner* — Jong-Suk (James) Lee
*Assistant Examiner* — Christopher E Dunay
(74) *Attorney, Agent, or Firm* — Maier & Maier, PLLC

(57) ABSTRACT

A UV panel light including a lamp housing, a UV module, a lighting module and the first control circuit; the lamp housing includes a metal plate body and two end covers, the metal plate body is bent, there are accommodating grooves on one surface of the metal plate body, there is a mounting groove on the other surface of the metal plate body, the end covers connect to the metal plate body, and the end covers cover two ends of several of the accommodating grooves. The UV module is provided in any of the accommodating grooves; the lighting module is provided in another the accommodating grooves; the first control circuit is provided in the mounting groove, connects electrically to the UV module and the lighting module and is used for the external power supply, which reduces the structural complexity and improves assembly efficiency of the UV panel light.

11 Claims, 7 Drawing Sheets

US 11,054,116 B1

UV PANEL LIGHT

CROSS-REFERENCE TO RELATED APPLICATIONS

The present patent application claims benefit and priority to Chinese Application No. 2020219341884 filed on Sep. 4, 2020 which is hereby incorporated by reference into the present disclosure.

TECHNICAL FIELD

The present relates to the technical field of germicidal equipment, particularly to a UV panel light.

BACKGROUND

Most existing UV germicidal panel lights are of a box structure which comprises the front housing and the rear housing, and the rear housing is usually made of several metal plates through welding, so the processing of the rear housing is complicated, the utilization of materials is low, the cost is high and the weight is heavy; In another aspect, the UV module and the lighting module are respectively installed in different cavities composed of the front housing and the rear housing, so the overall structure is relatively complicated.

The foregoing content is only used for assisting in understanding the technical scheme of the invention, but not mean the acknowledgement of that the above content is a prior art.

SUMMARY

The main objective of the present invention is to provide a UV panel light to reduce the structure complexity of UV panel lights and improve the assembly efficiency.

To realize the above objective, the UV panel light according to the present comprises:

the lamp housing comprises a metal plate body and two end covers, wherein, the metal plate body is bent for several times, there are several accommodating grooves on one surface of the metal plate body, there is a mounting groove on the other surface of the metal plate body, two the end covers connects to the metal plate body, and two the end covers cover respectively two ends of several the accommodating grooves;

The UV module which is provided in any one of the accommodating grooves;

a lighting module which is provided in another the accommodating grooves; and as for first control circuit, the first control circuit is provided in the mounting groove, connects electrically to the UV module and the lighting module and is used for the external power supply.

In one embodiment of this invention, both ends of any of the end covers are provided with a hoisting hole;

both ends of the metal plate body are provided with an avoidance space corresponding to the hoisting hole.

In one embodiment of this invention, the metal plate body has a length direction which is vertical to the extension direction of the accommodating groove;

both ends of the metal plate body in the length direction are provided with inclined planes, and each of the inclined planes and two the end covers work to form the avoidance space.

In one embodiment of this invention, the cross section of the accommodating groove is triangle or trapezoidal;

and/or, the cross section of the mounting groove is triangle or trapezoidal.

In one embodiment of this invention, the UV panel light comprises one mesh-shape cover plate which covers the opening of the accommodating groove corresponding to the UV module and is provided with several mesh holes;

both ends of the mesh-shape cover plate are against the surface of the surface of two the end covers facing the metal plate body.

In one embodiment of this invention, any of the end covers is provided with an avoidance opening which is corresponding to one end of the accommodating groove used for installing the UV module;

the UV panel light comprises a mesh-shape cover plate which covers the opening of the accommodating groove corresponding to the UV module, one end of the mesh-shape cover plate is against the surface of the end covers facing the metal plate body, the other end of the mesh-shape cover plate extends to the avoidance opening and is bent towards the end covers to form a bent part, the bent part is provided with a fixing hole, a screw passes through the fixing hole and connects to the end cover;

the mesh-shape cover plate is provided with several mesh holes.

In one embodiment of this invention, the UV panel light comprises a translucent cover plate which covers the opening of the accommodating groove corresponding to the lighting module, both ends of the translucent cover plate are against the surface of two the end covers facing the metal plate body.

In one embodiment of this invention, the UV panel light comprises a reflector which connects to the metal plate body and is between the UV module and the metal plate body;

the reflector is provided in a concave surface shape facing the surface of the UV module.

In one embodiment of this invention, the UV panel light also comprise the second control circuit provided in any of the accommodating grooves, the second control circuit comprises a mounting bracket and a circuit board, the mounting bracket connects to the bottom wall of the accommodating groove, the circuit board is provided in the mounting bracket, the circuit board is provided with a sensor, an adjusting switch and dimming interface, the sensor, the adjusting switch and the dimming interface are at least partially exposed to the opening of the accommodating groove.

In one embodiment of this invention, there are three the accommodating grooves on one surface of the metal plate body, and the three accommodating grooves are provided in parallel; the UV panel light comprises two the UV modules which are provided respectively in two the accommodating grooves on the periphery, the lighting module is provided in the middle the accommodating groove.

Or, there are three the accommodating grooves on one surface of the metal plate body, three the accommodating grooves are provided in parallel; the UV panel light comprises two the lighting modules which are provided respectively in two the accommodating grooves on the periphery, the UV module is provided in the middle the accommodating groove.

the lamp housing of the present invention comprises a metal plate body and two end covers, the metal plate body is bent for several times, there are several accommodating grooves and mounting grooves on two surfaces of the metal plate body, simplifying manufacturing of the metal plate body; and, two the end covers connect to the metal plate body, two the end covers cover both ends of several the accommodating grooves, enhancing the stability of the metal plate body. In another aspect, based on the integral metal plate body, the UV module and the lighting module are provided in two accommodating grooves respectively, the first control circuit is installed in the mounting groove, simplifying installation of the UV module, lighting module and the first control circuit, reducing the structure complexity of the UV panel light and improving the assembly efficiency. In addition, such a design can also improve the utilization rate of materials of the box body of the UV panel light, reduce the cost of materials and reduce the weight of the product.

BRIEF DESCRIPTION OF THE DRAWINGS

To better describe the technical schemes of the embodiments of present or prior art, a brief introduction of FIG. to be used in the descriptions of the embodiment or prior art is made hereby. Obviously, the attached drawing described below are only several embodiments of the present. For common technicians in this field, they can obtain other attached drawings. Based on these structures shown in the attached drawing without making additional creative endeavors.

The implementation, functional characteristics and advantages of the present will be further illustrated hereinafter in conjunction with the embodiments and accompanying attached drawing.

DETAILED DESCRIPTION

Combined with the attached drawing in the embodiments of the present, to clearly and completely describe the technical scheme of the embodiments of present. Obviously, only part of the embodiments of present (instead of all of the embodiment) are described here. Based on the embodiments of this present, all other embodiments acquired by the common technicians in this field without creative work, shall be in the protection scope of this present.

It should be noted that, if there is a directional indication (upper, lower, left, right, front, and rear, etc.) in the embodiments of the present, the directional indication is only used to explain the relative positional relationship, motion condition, etc. between the components in a particular position (as shown in the attached drawing), and if the particular attitude is changed, the directional indication is changed accordingly.

In addition, if there are descriptions relating to "first", "second" and the like in the embodiments of the present, such descriptions of "first", "second" and the like are for descriptive purposes only and are not to be construed as indicating or implying their relative importance or implying an indication of the number of indicated technical features. As such, a feature that defines as "first", "second" may explicitly or implicitly include at least one of that features. In addition, the "and/or" as stated in the whole text should be understood as there are three paralleled schemes where scheme A, or scheme B or scheme A and scheme B can be met at the same time (taking "A and/or B as an example"). In addition, the technical schemes of embodiments may be combined with each other, but must be available for common technicians in this field, and when the combination of the technical scheme is contradictory or impossible, it should be considered that the combination of the technical scheme does not exist and not fall within the scope of the present.

Figure 5:
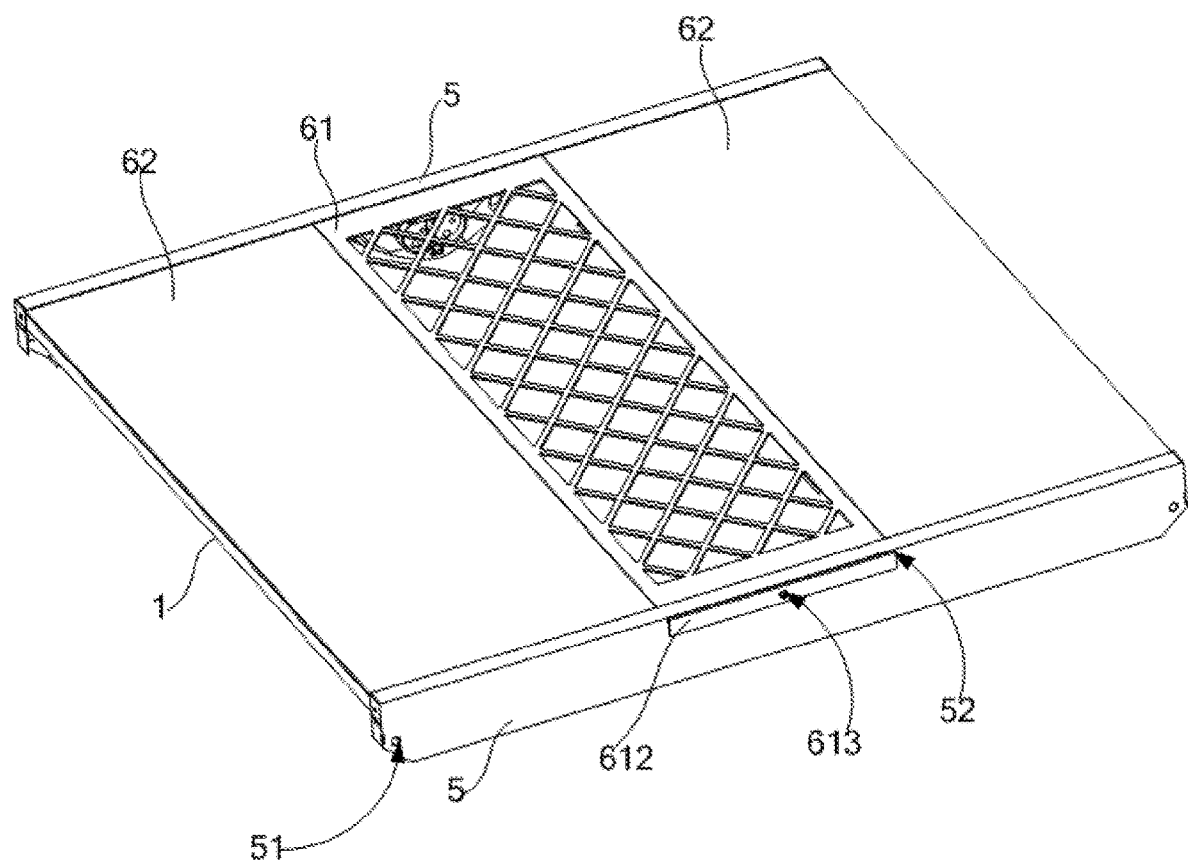
FIG. 5 is a schematic diagram showing the structure of another example of the UV panel light of the present.
Figure 6:
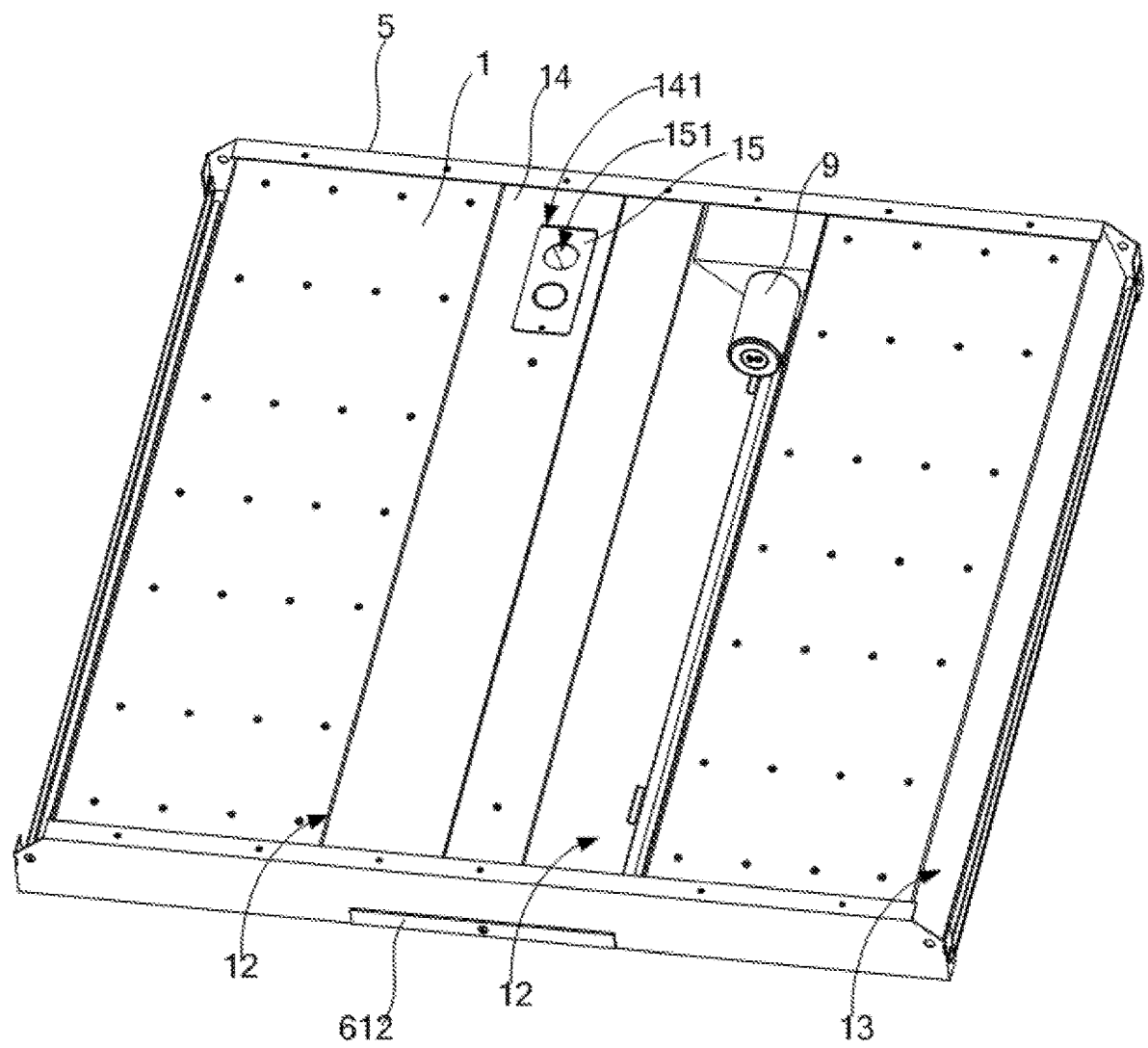
FIG. 6 is a schematic diagram showing the structure of another perspective of the UV panel light in FIG. 5.
Figure 7:
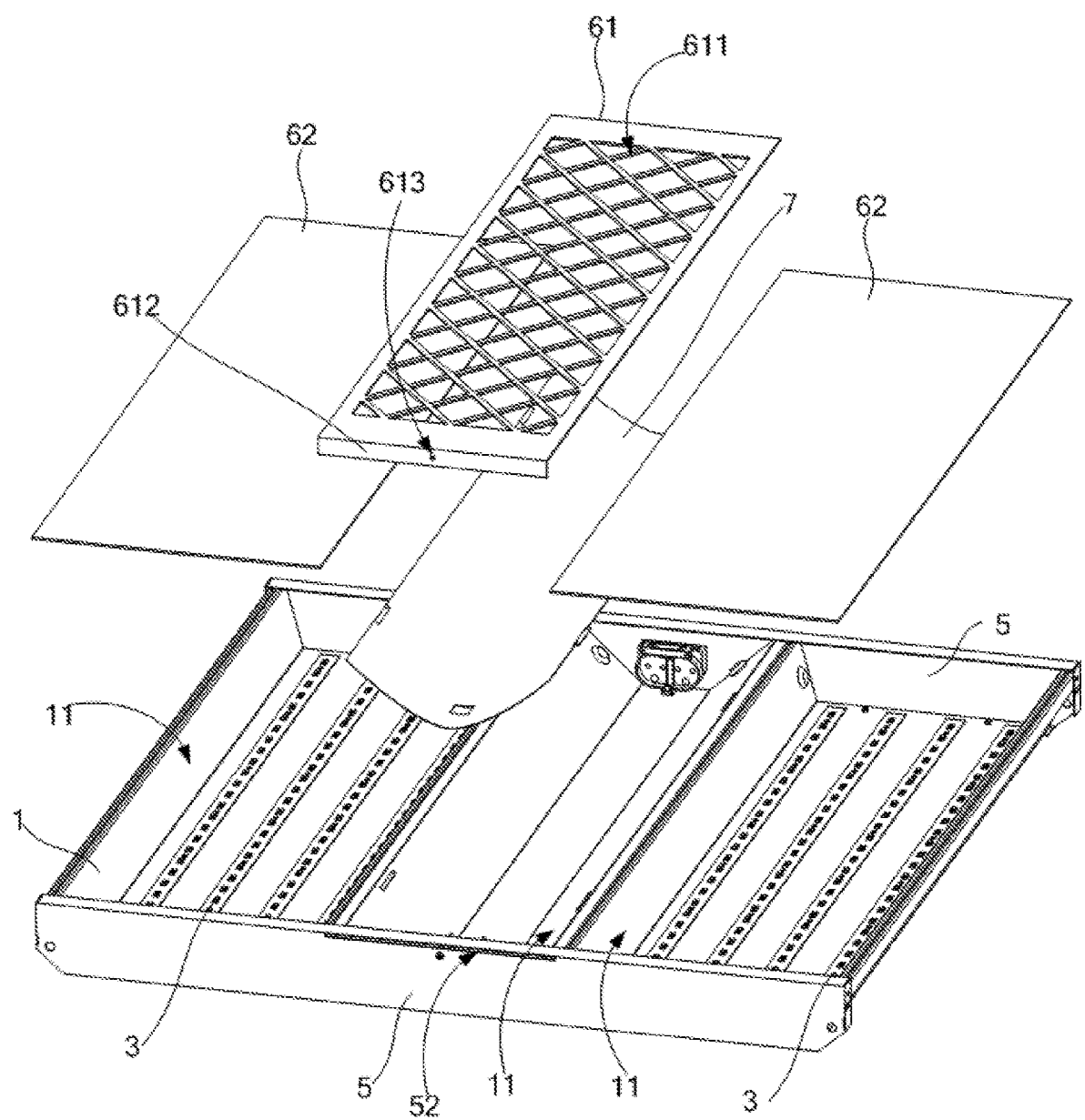
FIG. 7 is a schematic diagram showing the assembly structure of the UV panel light in FIG. 5.

The present provides a UV panel light. Details see FIG. 1, it is a schematic diagram showing the structure of an example of the UV panel light of the present; Refer to FIG. 2, it is a schematic diagram showing the sectional structure of the UV panel light in FIG. 1; Refer to FIG. 3 is the schematic diagram showing the assembly structure of UV panel light in FIG. 1; Refer to FIG. 4, it is a schematic diagram showing the assembly structure of another perspective of the UV panel light in FIG. 3; Refer to FIG. 5, it is a schematic diagram showing the structure of another example of the UV panel light of the present; Refer to FIG. 6, it is a schematic diagram showing the structure of another perspective of the UV panel light in FIG. 5; Refer to FIG. 7 is the schematic diagram showing the assembly structure of UV panel light in FIG. 5.

Figure 1:
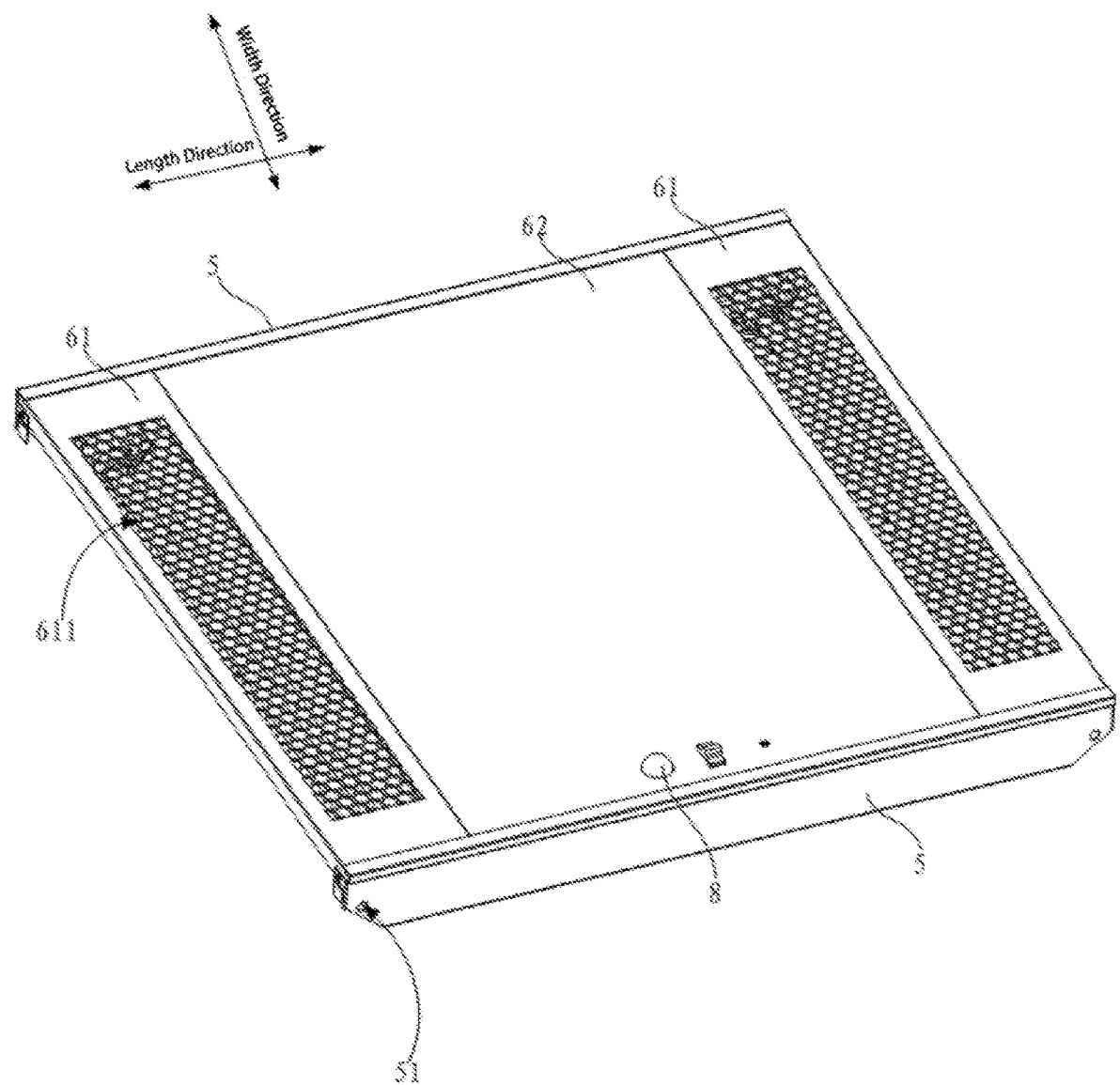
FIG. 1 is a schematic diagram showing the structure of an example of the UV panel light of the present.
Figure 2:
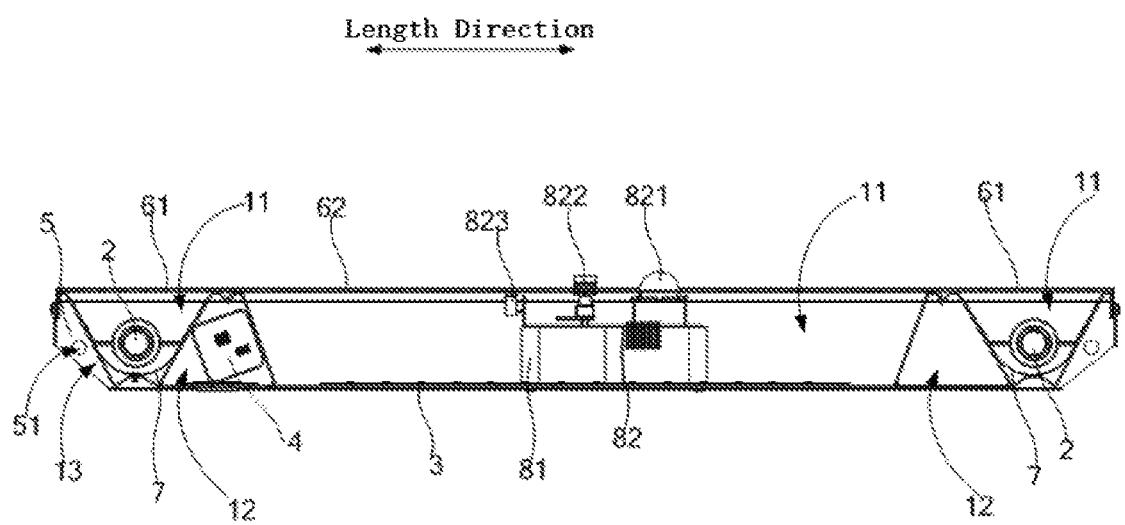
FIG. 2 is a schematic diagram showing the sectional structure of the UV panel light in FIG. 1.
Figure 3:
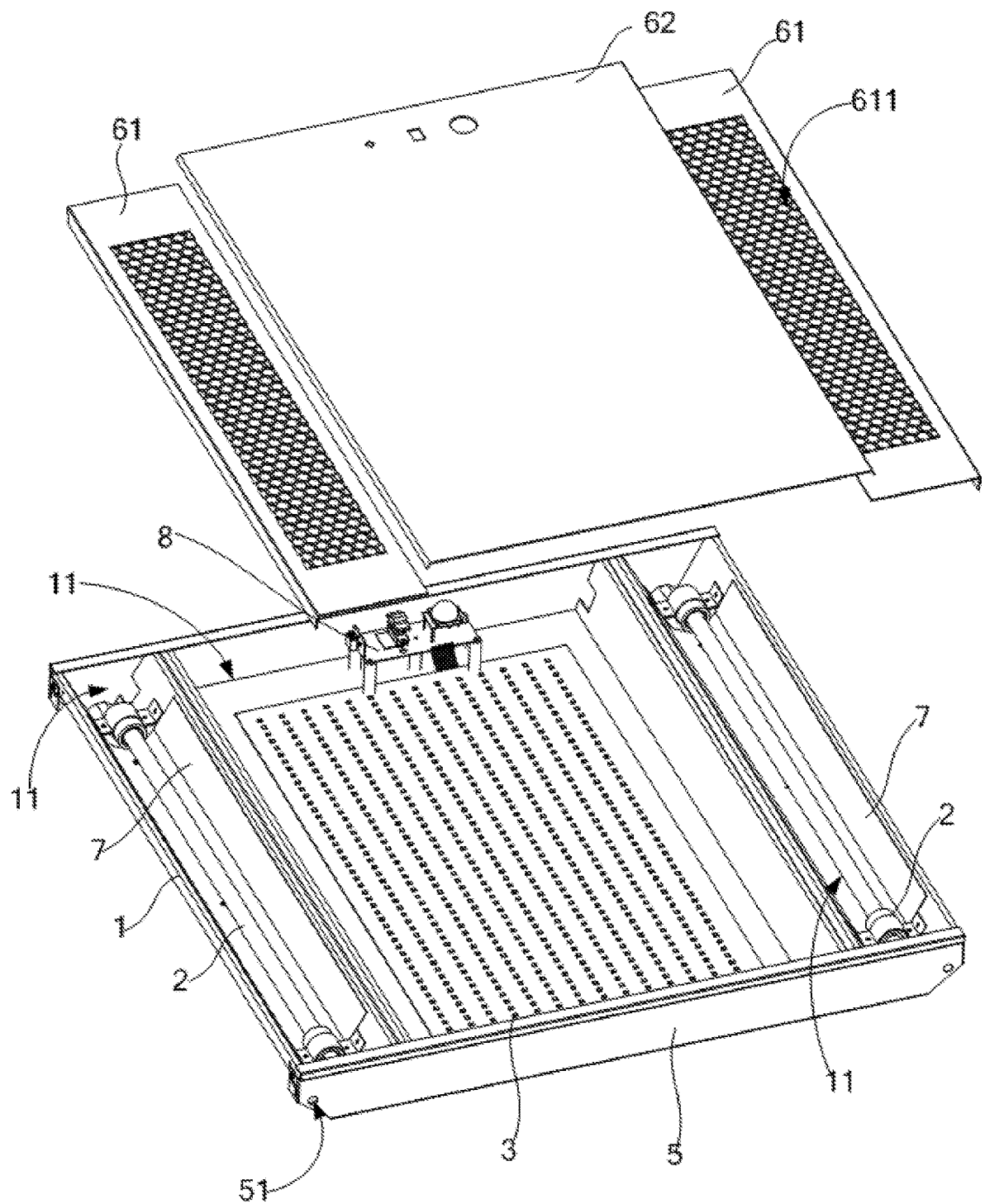
FIG. 3 is a schematic diagram showing the assembly structure of the UV panel light in FIG. 1.
Figure 4:
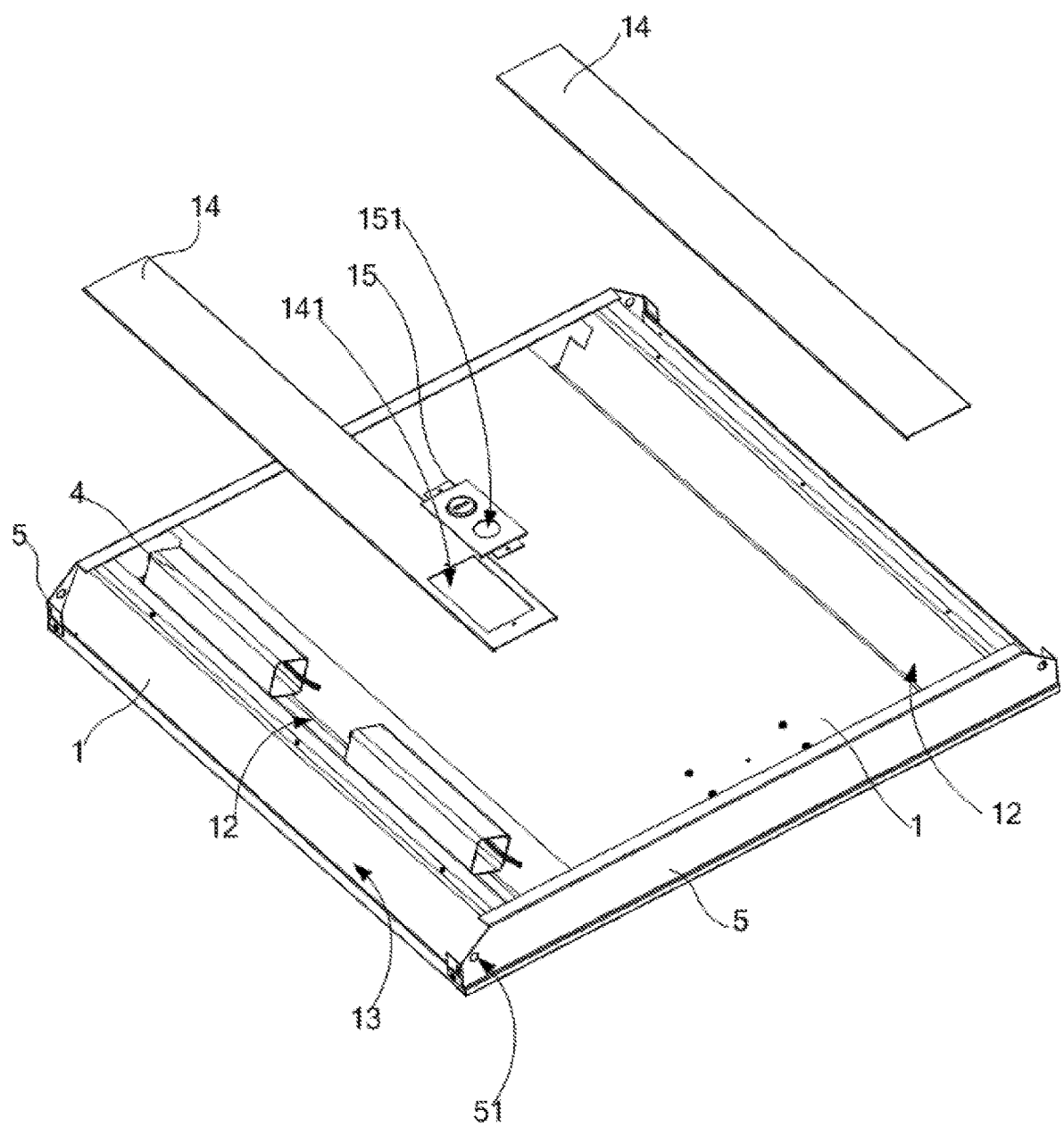
FIG. 4 is a schematic diagram showing the assembly structure of another perspective of the UV panel light in FIG. 3.

In the embodiment of the present, as shown in FIG. 1, and combined with FIG. 2, FIG. 3 and FIG. 4, the UV panel light includes: lamp housing, UV module 2, lighting module 3 and the first control circuit 4; a lamp housing which comprises a metal plate body 1 and two end covers 5, wherein, the metal plate body 1 is bent for several times, there are several accommodating grooves 11 on one surface of the metal plate body 1, there is a mounting groove 12 on the other surface of the metal plate body 1, two the end covers 5 connects to the metal plate body 1, and two the end covers 5 cover respectively two ends of several the accommodating grooves 11; UV module 2 is provided in any of accommodating grooves 11; lighting module 3 is provided in another accommodating groove 11; the first control circuit 4 is provided in mounting groove 12, the first control circuit 4 connects electrically to UV module 2 and lighting module 3, and the first control circuit 4 is used for external power supply.

In this embodiment, the lamp housing comprises the metal plate body 1 and two end covers 5, the metal plate body 1 is bent for several times and is manufactured with the extrusion forming process, there are several accommodating grooves 11 and mounting grooves 12 respectively on two surfaces of the metal plate body 1, simplifying the manufacturing process of the metal plate body 1; and, two end covers 5 connect to the metal plate body 1, two end covers 5 cover both ends of several accommodating grooves 11, enhancing the stability of the metal plate body 1 and improving the overall strength of the UV panel light. In another aspect, based on the integral metal plate body 1, the UV module 2 and the lighting module 3 are provided in two accommodating grooves 11 respectively, the first control circuit 4 is installed in the mounting groove 12, simplifying installation of the UV module 2, lighting module 3 and the first control circuit 4, reducing the structure complexity of the UV panel light and improving the assembly efficiency. In addition, such a design can also improve the utilization rate of materials of the box body of the UV panel light, reduce the cost of materials and reduce the weight of the product.

In one embodiment of this invention, two end covers 5 connect to the metal plate body 1, which can refer to that: metal plate body 1 has a length direction which spans several accommodating grooves 11 and mounting grooves 12; and the metal plate body 1 has a width direction which is parallel to the extension direction of accommodating grooves 11 and mounting grooves 12. Wherein, the length direction is vertical to the width direction.

During manufacturing of the metal plate body 1, the length direction of the metal plate body 1 is bent to form several accommodating grooves 11 and mounting grooves 12. Making a cross section on the length direction of the metal plate body 1, it can be considered that the cross section profile of the metal plate body 1 is one line segment, several accommodating grooves 11 and mounting grooves 12 are troughs on different phase positions of the metal plate body 1, wherein, the position of the opening of accommodating grooves 11 is the wave crest, and the position of the opening of mounting grooves 12 is also the wave crest. End covers 5 can connect in a fixing way to the wall where the wave crest is, enhancing the overall strength of the metal plate body 1.

Optionally, end covers 5 and the metal plate body 1 can be connected with screws.

Optionally, end covers 5 and the metal plate body 1 can be welded connection.

In one embodiment of this invention, end covers 5 can be made of metal plate. Understandably, one piece of metal plate is made through extrusion forming into a metal plate workpiece whose periphery has convex parts, simplifying manufacturing of end covers 5. In other words, end covers 5 comprise the plate body and convex parts on the periphery of the plate body. When end covers 5 connect to the metal plate body 1, convex parts connect to the metal plate body 1 in a fixing way, and the plate body is against the periphery of the metal plate body 1.

In one embodiment of this invention, as shown in FIG. 4 and FIG. 6, the lamp housing also comprises a rear cover 14 which connects to the metal plate body 1 and partially covers the opening of the mounting groove 12 corresponding to the first control circuit 4, preventing users from directly seeing the first control circuit 4 to improve the beauty of the UV panel light.

Optionally, the rear cover 14 is provided with mounting holes 141 connecting mounting grooves 12.

Optionally, the lamp housing also comprises a threading board 15 which connects to the peripheral wall of mounting holes 141 as an ornament of the UV panel light, and the threading board 15 is provided with a threading hole 151.

In one embodiment of this invention, as shown in FIG. 2 and FIG. 4, both ends of each end cover 5 are provided with a hoisting hole 51; Both ends of the metal plate body 1 are provided with an avoidance space 13 corresponding to the hoisting hole 51.

In this embodiment, both ends of each end cover 5 are provided with a hoisting hole 51, so that cables pass through the hoisting hole 51 and are bound with end covers 5 to realize hoisting of the UV panel light. In another aspect, the metal plate body 1 is provided with an avoidance space 13 corresponding to the hoisting hole 51, facilitating passing through of cables.

Wherein, since the metal plate body 1 is provided with an avoidance space 13 corresponding to the hoisting hole 51, the end cover 5 corresponding to the hoisting hole 51 will not protrude the periphery of the UV panel light, effectively improving the appearance smoothness of the UV panel light. In another aspect, such design can also prevent users to bend end covers 5, so that the hoisting hole 51 can get away from the mounting metal plate, cables can pass through the hoisting hole 51, users' secondary operation is reduced, and users' usage experience is improved.

In application of this embodiment, the UV panel light can be directly installed onto the ceiling or can be installed onto the ceiling with cables through hoisting.

When the UV panel light is directly installed to the mounting position of the ceiling, the periphery of the metal plate body 1 and/or end covers 5 can be against the periphery of the corresponding mounting position, facilitating positioning and installation of the UV panel light. The metal plate body 1 is provided with an avoidance space 13 corresponding to the hoisting hole 51, so both ends of end covers 5 will not protrude the periphery of the metal plate body 1, reducing the overall size of the UV panel light; and, when installing the UV panel light, if the mounting space above the ceiling is small, the UV panel light can be pushed obliquely upward into the mounting position, so that the UV panel light will not touch the skeleton of the ceiling when the UV panel light is pushed obliquely upward into the mounting position of the ceiling, improving the flexibility of mounting of the UV panel light.

In one embodiment of this invention, the avoidance space 13 can be a concave groove installed onto the metal plate; or, the avoidance space 13 is a space formed when the periphery of the mounting metal plate obliques towards the middle part of the metal plate body.

In one embodiment of this invention, metal plate body 1 has a length direction which is vertical to the extension direction of accommodating groove 11; both ends of the metal plate body 1 along its length direction are provided with an inclined plane, each of inclined planes work with two end covers 5 to form an avoidance space 13.

In this embodiment, both ends of the metal plate body 1 along its length direction are provided with an inclined plane, a chamfer structure can be formed on both ends of the UV panel light, avoiding accidents caused by contact of the UV lamp panel with the skeleton of the ceiling when installing the UV panel light; In another aspect, based on the structure of metal plate body 1 made through extrusion forming, the inner wall of the accommodating grooves 11 on the other surface of the metal plate body 1 is also an inclined plane, which can effectively enhance the light convergence function of the inner wall of accommodating grooves 11.

In one embodiment of this invention, the cross section of accommodating groove 11 is triangle or trapezoidal;

In this embodiment, the cross section of accommodating grooves 11 is triangle or trapezoidal. When the UV module 2 and/or the lighting module 3 are/is installed into the accommodating groove 11, the inner wall of the accommodating groove 11 will converge the rays of light of UV module 2 and/or lighting module 3. In other words, after rays of light generated by UV module 2 and/or lighting module 3 reach the inner wall of the accommodating groove 11, rays of light will be reflected to the area corresponding to the opening of the accommodating groove 11, realizing secondary utilization of light. In another aspect, the cross section of accommodating grooves 11 is triangle or trapezoidal, when end covers 5 on both ends partially cover one end of accommodating grooves 11, the inner wall of accommodating grooves 11 and the convex part of end covers 5 form a triangle structure, improving the tensile strength of the UV panel light.

In one embodiment of this invention, the cross section of mounting groove 12 is triangle or trapezoidal.

In this embodiment, under the premise of being able to form mounting grooves 12, the cross section of mounting grooves 12 is triangle or trapezoidal, which can reduce the occupation length of the bottom wall of the mounting groove 12 and then reduce consumption of materials used for manufacturing metal plate body 1. In another aspect, when end covers 5 on both ends partially cover one end of mounting grooves 12, the inner wall of mounting groove 12 and convex part of end covers 5 form a triangle structure, improving the tensile strength of the UV panel light.

In one embodiment of this invention, as shown in FIG. 3, the UV panel light comprises a mesh-shape cover plate 61 which covers the opening of the accommodating groove 11 corresponding to the UV module 2 and is provided with several mesh holes 611; both ends of the mesh-shape cover plate 61 are against the surface of two end covers 5 facing the metal plate body 1.

In this embodiment, both ends of the mesh-shape cover plate 61 are against the surface of two end covers 5 facing the metal plate body 1, the metal plate body 1 work with end covers 5, further fixing the mesh-shape cover plate 61 and improving the overall strength of the UV panel light.

Optionally, mesh-shape cover plate 61 and metal plate body 1 are connected through screws. In other words, after passing through the through hole of the mesh-shape cover plate 61, screws connect to the area corresponding to the opening of the accommodating grooves 11 of the metal plate body 1.

Optionally, mesh-shape cover plate 61 and end covers 5 are connected through screws. In other words, after passing through the convex part of end covers 5, screws connect to the through hole of the mesh-shape cover plate 61.

In one embodiment of this invention, as shown in FIG. 5, any one of end covers 5 is provided with an avoidance opening 52 which is corresponding to one end of the accommodating groove 11 used for installing UV module 2; the UV panel light comprises a mesh-shape cover plate 61 which covers the opening of the accommodating groove 11 corresponding to the UV module 2, one end of the mesh-shape cover plate 61 is against the surface of the end covers 5 facing the metal plate body 1, the other end of the mesh-shape cover plate 61 extends to the avoidance opening 52 and is bent towards the end covers 5 to form a bent part 612, the bent part 612 is provided with a fixing hole 613, a screw passes through the fixing hole 613 and connects to the end cover 5; mesh-shape cover plate 61 is provided with several mesh holes 611.

In this embodiment, end covers 5 are provided with an avoidance opening 52, when installing the mesh-shape cover plate 61, one end of the mesh-shape cover plate 61 can be inserted in the position between the end cover 5 and the metal plate body 1, and the other end of the mesh-shape cover plate 61 connects to the other end cover 5. In other words, after removing screws used for fixing mesh-shape cover plate 61 and end covers 5, one end of the mesh-shape cover plate 61 is free, so that the mesh-shape cover plate 61 can be installed and disassembled quickly and the maintenance efficiency of the UV panel light is improved.

In one embodiment of this invention, as shown in FIG. 3, the UV panel light comprises the translucent cover plate 62 which covers the opening of the accommodating groove 11 corresponding to the lighting module 3, both ends of the translucent cover plate 62 are against the surface of two end covers 5 facing the metal plate body 1.

In this embodiment, the translucent cover plate 62 covers the accommodating groove 11 corresponding to the lighting module 3, preventing external sundries entering into the lighting module 3, reducing the damage probability of the UV panel light and improving the service life of the UV panel light.

Optionally, the lighting module 3 comprises a LED lamp panel provided on the bottom wall of the accommodating grooves 11.

Optionally, the bottom wall of the accommodating groove 11 corresponding to the lighting module 3 can be adjusted according to the dimensions of the lighting module 3.

In one embodiment of this invention, as shown in FIG. 3 and FIG. 7, the UV panel light comprises the reflector 7 which connects to the metal plate body 1 and is provided between the UV module 2 and the metal plate body 1; reflector 7 is provided in a concave surface shape facing the surface of UV module 2.

In this embodiment, the area corresponding to the UV module 2 is provided with a reflector 7 which is provided in a concave surface shape facing the surface of the UV module 2, so that the UV rays generated by the UV module 2 can be reflected into the opening of the accommodating grooves 11 to improve the sterilization effect of the UV panel light.

Optionally, the surface of the reflector 7 is provided in a mirror shape.

Optionally, the UV module 2 comprises a terminal block provided in accommodating grooves 11 and a UV fluorescent tube connecting electrically to the terminal block.

In one embodiment of this invention, as shown in FIG. 2 and FIG. 3, the UV panel light also comprises the second control circuit 8 provided in any of accommodating grooves 11, second control circuit 8 comprises a mounting bracket 81 and a circuit board 82, mounting bracket 81 connects to the bottom wall of accommodating groove 11, circuit board 82 is provided on mounting bracket 81, circuit board 82 is provided with a sensor 821, an adjusting switch 822 and a dimming interface 823, sensor 821, the adjusting switch 822 and dimming interface 823 are at least partially exposed to the opening of accommodating groove 11.

In this embodiment, the circuit board 82 is provided with a sensor 821, an adjusting switch 822 and a dimming interface 823, it can be judged by virtue of the sensor 821 whether there is a human body in the area just facing the UV panel light, so that illumination or turning off of the UV module 2 can be adjusted; wherein, sensor 821 can be infrared sensor 821 or microwave sensor 821. In another aspect, the luminance, luminous intensity or the warm or cold colors of rays of light of the lighting module 3 can be adjusted through operating the adjusting switch 822. In yet another aspect, the dimming interface 823 can be introduced into the Bluetooth control module 9, so that users can connect the Bluetooth control module 9 through the intelligent terminal to adjust the working state of the UV panel light.

Optionally, the dimming interface 823 can be USB interface, 3.5 mm socket and type-c interface.

In this embodiment, the UV panel light also comprises a Bluetooth control module 9 which is provided in the mounting groove 12 and connects electrically to the second control circuit 8.

In one embodiment of this invention, as shown in FIG. 2 and FIG. 3, there are three accommodating grooves 11 on one surface of the metal plate body 1, and three accommodating grooves 11 are provided in parallel; UV panel light comprises two UV modules 2 which are provided respectively in two accommodating grooves 11 on the periphery, lighting module 3 is provided in the middle the accommodating grooves 11.

In this embodiment, the lighting module 3 is provided in the middle part, two UV modules 2 are provided on both sides of the lighting module 3, and the sterilization effect of the UV panel light can be improved through increasing the quantity of the UV module 2. In another aspect, large-size lighting module 3 can be selected as the case may be to improve the lightening intensity of the UV panel light.

In one embodiment of this invention, as shown in FIG. 5 and FIG. 7, there are three accommodating grooves 11 on one surface of the metal plate body 1, and three accommodating grooves 11 are provided in parallel; The UV panel light comprises two lighting modules 3 which are provided respectively in two accommodating grooves 11 on the periphery, and UV modules 2 are provided in the middle accommodating groove 11.

In this embodiment, the UV module 2 is provided in the middle part, two lighting modules 3 are provided on both sides of the lighting module 3, and the lighting effect of the UV panel light can be improved through increasing the quantity of the lighting module 3. In another aspect, large-power UV module 2 can be selected as the case may be to improve the sterilization effect of the UV panel light.

the description is only the preferred embodiment of the present, and it is not for this reason that the patent scope of the present is limited. Any equivalent structural transformation made by using the description of the present and the drawing, or direct/indirect application in other related innovation technical fields under the inventive concept of the present, is included in the patent protection scope of the present.

What is claimed is:

1. An ultraviolet panel light comprising:
    a lamp housing formed from a metal plate body and which is connected to two end covers, at least one mesh-shaped cover plate, at least one translucent cover plate, and at least one rear cover plate,
    wherein the metal plate body is bent several times to form several accommodating grooves on one surface of the metal plate body with at least one mounting groove correspondingly formed on another surface of the metal plate body between each of the several accommodating grooves;
    wherein the two end covers cap, respectively, each end of the several accommodating grooves and the at least one mounting groove;
    wherein at least one of the several accommodating grooves house an ultraviolet module and is enclosed on a front side by the at least one mesh-shaped cover plate;
    wherein at least one of the several accommodating grooves house a lighting module and is enclosed on the front side by the at least one translucent cover plate;
    wherein the at least one mounting groove is covered by the at least one rear cover plate;
    wherein the at least one mesh-shaped cover plate and the two end covers are removable so as to facilitate replacement of the ultraviolet module; and
    wherein both the ultraviolet module and the lighting module are directed so as to selectively illuminate an illumination area exterior to the ultraviolet panel light.

2. The ultraviolet panel light as claimed in claim 1, wherein both ends of any of the end covers are provided with a hoisting hole; and
    both ends of the metal plate body are provided with an avoidance space corresponding to the hoisting hole.

3. The ultraviolet panel light as claimed in claim 2, wherein the metal plate body has a length direction which is vertical to an extension direction of the accommodating groove; and
    both ends of the metal plate body in the length direction are provided with inclined planes, and each of the inclined planes and two end covers work to form the avoidance space.

4. The ultraviolet panel light as claimed in claim 1, wherein a cross section of the accommodating grooves is triangle or trapezoidal; and/or
    the cross section of the mounting groove is triangle or trapezoidal.

5. The ultraviolet panel light as claimed in claim 1, wherein
    both ends of the at least one mesh-shaped cover plate are against a surface of the two the end covers facing the metal plate body.

6. The ultraviolet panel light as claimed in claim 1, wherein any of the end covers is provided with an avoidance opening which is provided on one end of the accommodating groove housing the ultraviolet module;
    one end of the at least one mesh-shaped cover plate abuts against a surface of the end covers facing the metal plate body, the other end of the at least one mesh-shaped cover plate extends to the avoidance opening and is bent towards the end covers to form a bent part, the bent part is provided with a fixing hole, a screw passes through the fixing hole and connects to the end cover; and
    the at least one mesh-shaped cover plate is provided with several mesh holes.

7. The ultraviolet panel light as claimed in claim 1, wherein the ultraviolet panel light comprises a translucent cover plate which covers the opening of the accommodating groove housing the lighting module, and both ends of the translucent cover plate are against a surface of two the end covers facing the metal plate body.

8. The ultraviolet panel light as claimed in claim 1, wherein the ultraviolet panel light comprises a reflector which connects to the metal plate body and is provided between the ultraviolet module and the metal plate body; and
    the reflector is provided in a concave surface shape facing the surface of the ultraviolet module.

9. The ultraviolet panel light as claimed in claim 1, wherein the ultraviolet panel light further comprises a second control circuit provided in any of the accommodating grooves, the second control circuit comprises a mounting bracket and a circuit board, the mounting bracket connects to the bottom wall of the accommodating groove, the circuit board is provided on the mounting bracket, the circuit board is provided with a sensor, an adjusting switch and a dimming interface, the sensor, the adjusting switch, and the dimming interface are at least partially exposed to the opening of the accommodating groove.

10. The ultraviolet panel light as claimed in claim 1, wherein there are three accommodating grooves on one surface of the metal plate body and the three accommodating grooves are provided in parallel; the ultraviolet panel light comprises two ultraviolet modules which are provided respectively in two of the three accommodating grooves on a periphery and the lighting module is provided in a middle of the three accommodating grooves.

11. The ultraviolet panel light as claimed in claim 1, wherein there are three accommodating grooves on one surface of the metal plate body and the three accommodating grooves are provided in parallel; the ultraviolet panel light comprises two lighting modules which are provided respectively in two of the three accommodating grooves on a periphery and the ultraviolet module is provided in a middle of the three accommodating grooves.

\* \* \* \* \*